(12) United States Patent
Kartheus et al.

(10) Patent No.: US 7,115,792 B2
(45) Date of Patent: Oct. 3, 2006

(54) SCAR-REDUCING PLASTER

(75) Inventors: Holger Kartheus, Hamburg (DE);
Carsten Hartkopf, Hamburg (DE);
Thorsten Berg, Hamburg (DE); Jan Jänichen, Hamburg (DE); Ulrich Köhler, Hamburg (DE)

(73) Assignee: Beiersdorf AG, Hamburg (DE)

( * ) Notice: Subject to any disclaimer, the term of this patent is extended or adjusted under 35 U.S.C. 154(b) by 105 days.

(21) Appl. No.: 10/948,622

(22) Filed: Sep. 22, 2004

(65) Prior Publication Data

US 2005/0095276 A1    May 5, 2005

Related U.S. Application Data

(63) Continuation of application No. PCT/EP03/02951, filed on Mar. 21, 2003.

(30) Foreign Application Priority Data

Mar. 22, 2002  (DE)  ............... 102 12 866

(51) Int. Cl.
*A61F 13/00*   (2006.01)
(52) U.S. Cl. ............ 602/48; 602/41; 602/42; 602/43; 602/54
(58) Field of Classification Search ............ 602/41–43, 602/46, 48, 52, 56; 604/304–308
See application file for complete search history.

(56) References Cited

U.S. PATENT DOCUMENTS

| | | |
|---|---|---|
| 4,661,099 A | 4/1987 | von Bittera et al. |
| 4,867,748 A | 9/1989 | Samuelsen |
| 5,527,535 A | 6/1996 | Guillemet |
| 5,844,013 A | 12/1998 | Kenndoff et al. |
| 5,891,076 A | 4/1999 | Fabo |
| 6,191,216 B1 | 2/2001 | Ganster et al. |
| 6,616,793 B1 | 9/2003 | Kartheus et al. |
| 6,878,385 B1 | 4/2005 | Jensen et al. |
| 2002/0160037 A1 | 10/2002 | Ahrens et al. |

FOREIGN PATENT DOCUMENTS

| | | |
|---|---|---|
| DE | 31 03 499 A1 | 8/1982 |
| DE | 31 03 500 A1 | 8/1982 |
| DE | 37 13 601 A1 | 11/1988 |
| DE | 42 33 289 A1 | 4/1994 |
| EP | 0 919 211 A2 | 6/1999 |
| WO | WO 92/05755 | 4/1992 |
| WO | WO 96/29035 | 9/1996 |

OTHER PUBLICATIONS

International Search Report from International Application No. PCT/EP03/02951 dated Nov. 7, 2003.

*Primary Examiner*—Kim M. Lewis
(74) *Attorney, Agent, or Firm*—Alston & Bird LLP

(57) ABSTRACT

The present invention is a scar-reducing plaster and a method for preparing scar-reducing plasters. The scar-reducing plasters comprise a backing film comprising an air- and water vapor-pervious and water-impervious polymer layer, and a breathable and adhesive polyurethane xerogel matrix layer that coats the backing film. The polyurethane xerogel matrix layer includes a central scar contact region and an edge region, wherein the scar contact region merges with the edge region and the thickness of the edge region decreases from the scar contact region to a thickness of from 5 to 150 μm at the edge of the polyurethane xerogel matrix layer. The scar-reducing plasters of the present invention have a reduced tendency to peel off during normal use.

16 Claims, 2 Drawing Sheets

SCAR-REDUCING PLASTER

CROSS-REFERENCE TO RELATED APPLICATIONS

This application is a continuation of PCT/EP03/02951, filed Mar. 21, 2003, which is incorporated herein by reference in its entirety, and also claims the benefit of German Priority Application No. 102 12 866.9, filed Mar. 22, 2002.

FIELD OF THE INVENTION

The invention relates to scar-reducing plasters, to the processes for their production and to the use thereof. The scar-reducing plasters comprise a backing film composed of an air- and water vapor-pervious and water-impervious polymer layer, a scar contact material, composed of a breathable and adhesive polyurethane xerogel matrix, where the backing film is coated over the whole area with the polyurethane matrix. In a particular embodiment, an edge layer is formed from the same polyurethane xerogel matrix, which is beveled to a thickness not exceeding 5 to 150 μm at the edge. The tendency of conventional scar dressings to peel off, caused by clothing, bed sheets, skin contact or during washing, is greatly reduced thereby. This in turn makes it possible for the first time for the scar plaster to be worn for the long duration of scar treatment without additional fixing sections.

BACKGROUND OF THE INVENTION

The body responds to a bleeding skin wound by stopping the invasion of pathogens and arresting the bleeding. Once this has occurred it is necessary to remove foreign bodies and tissue detritus and construct new tissue. The normal wound-healing process can be divided for simplicity into 4 phases:
1. vascular reaction and blood clotting,
2. inflammation,
3. new tissue formation (formation of granulation tissue and reepithelialization), and
4. remodeling.

These processes overlap and are partly mutually dependent, so that the sequence only approximately corresponds to the time course of wound healing.

The vascular reaction phase has the function of preventing major blood losses and entails vasoconstriction, which persists until blood clotting provisionally closes the wound. The processes taking place in the inflammation phase are predominantly catabolic, i.e. breaking down. In this phase of wound healing, granulocytes, macrophages and lymphocytes clean the wound by taking up exogenous material and tissue detritus and breaking it down enzymatically.

The phase of new tissue formation by contrast includes repair, i.e. anabolic responses. An adequate blood supply is a precondition for a wound to heal well, so that new blood vessels are formed (angiogenesis) from as early as the third day after the injury. New connective tissue formation takes place in parallel with the vascularization. Fibroblasts migrate along the fibrin matrix into the wound. They produce the connective tissue ground substance consisting of proteoglycans and collagen fibers, which are crucial for tissue strength.

In healthy tissue, collagen fibers are aligned in particular patterns which follow the main directions of tension. The presence of coenzymes and cofactors such as, for example, ascorbic acid, iron and copper is crucial for collagen synthesis. If there is a deficiency of these substances, wound healing may be impaired. Scar tissue results in this case, being characterized by an unorganized structure of the collagen fibers.

The outgrowth of connective tissue takes place to the same extent as the breakdown of the provisional fibrin matrix (fibrinolysis) and the recanalization again of the closed vessels. The mitotic activity of the fibroblasts terminates with new fiber formation. They are converted on the one hand into fibrocytes, and on the other hand into myofibroblasts. The latter contain contractile elements and are able to contract. In this case, the collagen fibers are tightened and—where possible—aligned according to the main direction of tension of the tissue. As a consequence thereof, the skin tissue which is capable of functioning contracts at the edge of the wound so that only a small defect then remains.

Wound healing requires a balanced equilibrium of contrary actions such as cell proliferation and cell apoptosis, construction and breakdown of blood vessels, and construction and breakdown of collagen. If this equilibrium—especially in the construction and breakdown of collagen fibers—is disturbed in any way it may lead to a hypotrophic, atrophic or hypertrophic scar. The events differentiating normal wound healing from, for example, hypertrophic wound healing start even during development of granulation tissue. The most visible difference in the tissue is the amount and orientation of the collagen fibers. In hypertrophic scar formation, an excess of collagen is produced, and the granulation tissue shows a tendency to construct the collagen fibers in a random and disordered manner.

Hypertrophic scars are raised relative to the surrounding skin and show a large number of variations in size, shape, color and consistency. These characteristics depend firstly on the site and size of the injury and secondly on the chronological development and the personal susceptibility. The ends are normally prominent and end abruptly, sometimes with finger-like projections. The reddish color and the swelling of fresh scars derives from the increased vessel density. Over time, the connective tissue tightens during the remodeling phase, and the blood vessel density declines. The scar therefore sinks somewhat and becomes paler. The remodeling process comprises remodeling of the scar tissue and is the phase of wound healing which lasts longest and may extend for up to 20 years after the injury. This essentially entails restructuring of the collagen fibers, with some of them being broken down by collagenases present in the tissue or else being newly crosslinked.

The general prior art on dressings and wound plasters says nothing about the specific problems arising in the treatment of scars. Thus, EP 0 264 299 B1 discloses a dressing consisting of a water-absorbing sealing pad which in turn is formed by one or more hydrocolloids. The hydrocolloid(s) are dissolved in a binder or mixed therewith.

The pad is firmly and completely gripped by a water-tight cover layer. The pad is, according to the invention, beveled at least around the outer periphery in such a way that the thickness at the edge does not exceed about one quarter of its maximum thickness. Production takes place by a dicasting process under high pressures and at high temperatures. This process is unsuitable for crosslinked polymer gels, for example polyurethane gels.

WO 92/05755 relates to contoured wound contact materials with an adhesive composition layer consisting of swellable hydrocolloids and water-insoluble, viscous constituents, for example, polyisobutylene, rubber, silicone or polyurethane elastomers. In this case, the adhesive composition layer in the edge zone, which layer is of the same type as the adhesive composition in the central zone, has a thickness of less than 0.5 mm (preferably less than 0.3 mm) and a width of at least 5 mm (preferably at least 10 mm). The hydrocolloid-based adhesive composition shows tack even on a moist substrate.

Foam wound contact materials as are obtainable for example from S & N under the name Cutinova® thin and Cutinova® hydro are inter alia described in DE 42 33 289 A1, in DE 196 18 825 A1 and WO 97/43328. The flat polyurethane foam with a thickness of from 1 to 6 mm is covered on one side by a polyurethane film. Plasters of appropriate size are cut out of the baled product. The wound contact material produced in this way surprisingly adheres completely on uptake of wound fluid and moreover does not show the known tendency of hydrocolloids to disintegrate on pronounced swelling, which may lead to residues of the hydrocolloid remaining in the wound.

The large-area wound contact materials which have been cut out are outstandingly suitable for managing chronic or poorly healing wounds of patients requiring hospital care. There is no discussion of a positive or negative effect on scar treatment. In particular, on mechanical stress the product easily peels off because of its cut edges. On contact with moisture, the open cut edges prove to be disadvantageous because water can thereby reach the absorbent layer and leads to swelling and adhesion of the polyurethane foam through penetration of moisture in from the side.

In addition, the significant height of the product (up to 4 mm) and the identical self-adhesive properties at the edge favors the adhesion of dirt and peeling off to adhesion of, for example, items of clothing.

A process for producing a dressing with thin edges consisting of at least two adhesive composition layers is described in EP 0 680 299 A1. The adhesive layers, which may be of the same type or differ in type, correspond to an arrangement of different areas which are connected together and which decrease in size towards the top. Moreover, the individual layers have a stepped profile which, in order to achieve an externally continuous outline, must be covered with a further layer. A further disadvantage is the stepwise slope of the dressing on the side facing the skin, so that contact is irregular thereby at some places in the wound region and wound edge region.

EP 0 919 211 A2 mentions the production of wound dressings with beveled edges from thermoformed plastics backing films which are release coated and have a cavity into which a self-adhesive hydrophilic polymer gel is introduced. The dressings have an adhesive covering layer which is in turn covered with a protective layer. The process is complicated and is unsuitable for wound dressings of "a piece". In this case too, the dressings are beveled on the side facing the wound.

Finally, mention may also be made of conventional plasters for the care of wounds (for example the fabric plaster Hansaplast® classic from Beiersdorf), which are only conditionally suitable for use as scar plasters. Disadvantages which emerge are the low elasticity and the tendency for the backing material to peel off at the edges of the plaster on mechanical stress when worn for a lengthy period. In addition, the plaster becomes thoroughly wet during daily ablutions or during hand washing and loses adhesiveness. Conventional plasters are visually very conspicuous, impede movements and impair for example the wear comfort in shoes.

Scar dressings differ from known wound care dressings and plasters in being left on the skin over a prolonged period in order to ensure a desired reducing effect. The usual thickness of wound plasters of about 1 mm and more leads with this long duration of wearing to detachment through friction on clothing, bed sheets, skin contacts or during daily washing. For this reason, known dressings or plasters cannot be employed for the indicated purpose. Moreover, the requirements to be met by the scar contact material are quite different from those for wound contact materials.

Scar coverings based on silicone gel, as are described, for example in EP 782457 A1, have the disadvantage that their breathability is lower and they are prone to maceration effects.

The maceration effects are moreover only one disadvantage shown by many known adhesive dressings. The problem with scar-reducing plasters is, on the one hand, skin-kindly and long-lasting adhesion to the skin, and on the other hand painless detachment from the skin without residues. None of the disclosures mentioned provides a proposed solution to this which is acceptable for the manufacturer and for the user.

SUMMARY OF THE INVENTION

One object of the present invention is therefore to eliminate the disadvantages of the prior art. In particular, the object of the present invention is to provide a scar-reducing plaster that makes regression of hyperthropic scars possible, ensures a skin-kindly, long-lasting adhesion, can be detached painlessly and without residues, and shows a greatly reduced tendency to peel off at the adhesive edges, in order thus to achieve a long duration of wearing without impairing the scar reduction. An additional intention is to provide a scar plaster which can be produced in a simple and cost-saving manner and that enriches the art.

The objects are achieved through the use of a plaster as scar-reducing plaster in accordance with the main claims. The dependent claims relate to advantageous embodiments of the plaster of the invention. The invention further includes the process for producing scar-reducing plasters.

It was surprising and not predictable for the skilled worker that the use of a plaster as scar-reducing plaster for the treatment of hypothropic scars, comprising a backing film composed of air- and water vapor-pervious and water-impervious polymer layer and a scar contact material composed of a breathable and adhesive polyurethane xerogel matrix, where the backing film is coated over the whole area with the polyurethane matrix, an edge layer is formed from polyurethane xerogel matrix, the scar contact material and the edge layer consist of the same polyurethane xerogel matrix, the edge layer slopes to a thickness not exceeding 5 to 150 µm at the edge, and the scar contact material located in the center merges continuously with the edge layer, remedy the disadvantages of the prior art.

The scar contact material of the plaster of the invention may have a thickness of from 0.2 to 2 mm, in particular from 0.5 to 1.5 mm.

DETAILED DESCRIPTION OF THE PREFERRED EMBODIMENTS

Figure 1:
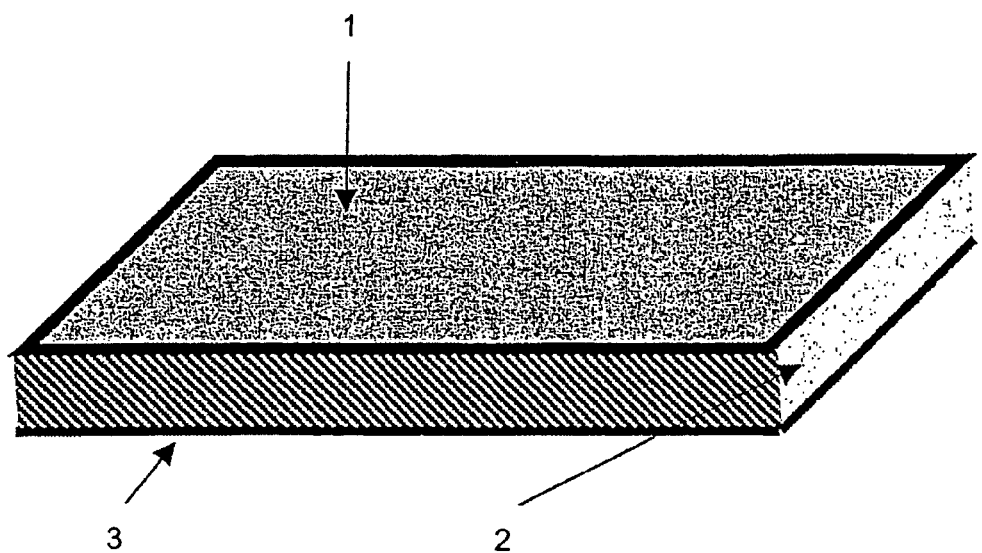
FIG. 1 provides one embodiment of the present invention illustrating the covering material and the backing film, wherein the backing film is coated with the polyurethane xerogel matrix.

The backing film, as is known from the prior art, consists of an air- and water vapor-pervious but water-impervious polymer layer having a thickness of about 10 to 100 µm. The optionally flexible backing film preferably consists of polymers from polyurethane, polyethylene (PE), polypropylene (PP), polyamide, polyester or polyether-ester.

Xerogels are gels which have lost their fluidity through various forms of treatment, evaporation, aspiration, etc. and characterize a limiting state to solids. The polyurethane xerogels used are therefore to be regarded in particular as anhydrous.

DE 196 18 825 relates to suitable polyurethane xerogels as matrix and discloses hydrophilic, self-adhesive polyurethane gels which consist of
   a) polyetherpolyols having 2 to 6 hydroxyl groups and OH numbers of from 20 to 112 and an ethylene oxide (EO) content of $\geq 10\%$ by weight,
   b) antioxidants,
   c) bismuth(III) carboxylates based on carboxylic acids having 2 to 18 C atoms and soluble in the polyols a), as catalysts, and
   d) hexamethylene diisocyanate, with a product of the functionalities of the polyurethane-forming components a) and d) of at least 5.2, where the amount of catalyst c) is from 0.005 to 0.25% by weight based on the polyol a), the amount of antioxidants b) is in the range from 0.1 to 1.0% by weight based on polyol a), and a ratio of free NCO groups of component d) to free OH groups of component a) (isocyanate index) is chosen in the range from 0.30 to 0.70.

Polyetherpolyols preferably having 3 to 4, very particularly preferably 4, hydroxyl groups and having an OH number in the range from 20 to 112, preferably 30 to 56, are employed. The ethylene oxide content in the polyetherpolyols employed according to the invention is preferably $\geq 20\%$ by weight.

The polyetherpolyols are known as such per se and are prepared by self-polymerization of epoxides such as ethylene oxide, propylene oxide, butylene oxide or tetrahydrofuran, or by addition of these epoxides, preferably of ethylene oxide and propylene oxide—where appropriate mixed together or separately and consecutively—onto starter components having at least two reactive hydrogen atoms, such as water, ethylene glycol, propylene glycol, diethylene glycol, dipropylene glycol, glycerol, trimethylolpropane, pentaerythritol, sorbitol or sucrose. Representatives of the high molecular weight polyhydroxy compounds mentioned for use are listed for example in High Polymers, Vol. XVI, "Polyurethanes, Chemistry and Technology" (Saunders-Frisch, Interscience Publishers, New York, Vol. 1, 1962, pages 32–42).

The isocyanate component employed is monomeric or trimerized hexamethylene diisocyanate, or hexamethylene diisocyanate which has been modified by biuret, uretdione, allophanate groups or by prepolymerization with polyetherpolyols or mixtures of polyetherpolyols based on known starter components having 2 or >2 reactive H atoms and epoxides such as ethylene oxide or propylene oxide of an OH number of $\leq 850$, preferably 100 to 600. The use of modified hexamethylene diisocyanate is preferred, in particular hexamethylene diisocyanate modified by prepolymerization with polyetherdiols of OH number 200 to 600. It is very particularly preferred for the hexamethylene diisocyanate to be modified with polyetherdiols of OH number 200–600 whose residual content of monomeric hexamethylene diisocyanate is below 0.5% by weight.

Suitable catalysts for the polyurethane gels of the invention are bismuth(III) carboxylates which are based on linear, branched, saturated or unsaturated carboxylic acids having 2 to 18, preferably 6 to 18, C atoms and which are soluble in the anhydrous polyetherpolyols a). Bi(III) salts of branched saturated carboxylic acids having tertiary carboxyl groups, such as 2,2-dimethyloctanoic acid (for example Versatic acids, Shell), are preferred. Preparations of these Bi(III) salts in excess proportions of these carboxylic acids are very suitable. A solution of 1 mol of the Bi(III) salt of Versatic 10 acid (2,2-dimethyloctanoic acid) in an excess of 3 mol of this acid with a Bi content of about 17% has proved outstandingly suitable.

The catalysts are preferably employed in amounts of from 0.03 to 0.1% by weight based on the polyol a).

Antioxidants suitable for the polyurethane xerogels of the invention are, in particular, sterically hindered phenolic stabilizers such as BHT (2,6-di-tert-butyl-4-methylphenol), Vulkanox BKF (2,2 min-methylenebis(6-tert-butyl-4-methylphenol) (Bayer AG), Irganox 1010 (pentaerythrityl tetrakis [3-(3,5-ditert-butyl-4-hydroxyphenyl)propionate]), Irganox 1076 (octadecyl 3-(3,5-ditert-butyl-4-hydroxyphenyl)propionate) (Ciba-Geigy) or tocopherol (vitamin E). Those of the α-tocopherol type are preferably employed.

The antioxidants are preferably employed in amounts of from 0.15 to 0.5% by weight based on the polyol a).

The isocyanate index (ratio of the free NCO groups employed in the reaction to the free OH groups) of the polyurethane xerogel compositions of the invention is, depending on the functionality of the isocyanate and polyol components employed, in the range from 0.30 to 0.70, preferably in the range from 0.45 to 0.60. The isocyanate index necessary for gel formation can be estimated very simply from the following formula:

$$f_{(polyol)} \bullet (f_{(isocyanate)} - 1) \bullet \text{index} \approx 2$$

$$\text{index} \approx \frac{2}{f_{(polyol)} \bullet (f_{(isocyanate)} - 1)}$$

wherein f is the functionality of the isocyanate or polyol component.

The isocyanate index actually to be used may vary by up to +20% from the calculated value depending on the desired tack or elasticity of the gel. The polyurethane xerogel compositions of the invention are prepared by conventional processes as described, for example, in Becker/Braun, Kunststoff-Handbuch, Vol. 7, polyurethane, pages 121 et seq., Carl-Hauser, 1983.

Further polyurethanes which are preferably employed are those disclosed in EP 0 665 856 B1. The hydrophilic polyurethanes are obtainable according to this from
1. a polyurethane xerogel which comprises
   (A) 25–62% by weight, preferably 30–60% by weight, particularly preferably 40–57% by weight, based on the total of (A) and (B), of a covalently crosslinked polyurethane as high molecular weight matrix and (B) 75–38% by weight, preferably 70–40% by weight, particularly preferably 60–43% by weight, based on the total of (A) and (B), of one or more polyhydroxyl compounds which are firmly bound in the matrix by secondary valence forces and have an average molecular weight between 1000 and 12 000, preferably between 1500 and 8000, particularly preferably between 2000 and 6000, and an average OH number between 20 and 112, preferably between 25 and 84, particularly preferably between 28 and 56, as liquid dispersant, the dispersant being essentially free of hydroxyl compounds with a molecular weight below 800, preferably below 1000, particularly preferably below 1500, and, where appropriate, (C) 0–100% by weight, based on the total of (A) and (B), of fillers and/or additives, and which is obtainable by reacting a mixture of
   a) one or more polyisocyanates,
   b) one or more polyhydroxyl compounds with an average molecular weight between 1000 and 12 000, and with an average OH number between 20 and 112,
   c) where appropriate catalysts or accelerators for the reaction between isocyanate groups and hydroxyl groups and, where appropriate,
   d) fillers and additives known per se from polyurethane chemistry, this mixture being essentially free of hydroxyl compounds with a molecular weight below 800, the average functionality of the polyisocyanates ($F_I$) being between 2 and 4, the average functionality of the polyhydroxyl compound ($F_P$) being between 3 and 6, and the isocyanate index (K) being given by the formula $$K = \frac{300 \pm X}{(F_1 \bullet F_P) - 1} + 7$$

in which $X \leq 120$, preferably $X \leq 100$, particularly preferably $X \leq 90$, and the index K has values between 15 and 70, where the stated averages of molecular weight and OH number are to be understood as number averages, 2. a water-absorbing material, and/or
3. a non-aqueous foaming agent.

The polyurethane gels can be prepared from the starting compounds known in polyurethane chemistry by processes known per se, as described for example in DE 31 03 499 A1, DE 31 03 500 A1 and EP 0 147 588 A1. However, it is essential that the above-defined conditions are complied with in the selection of the yellow-forming components because, otherwise, tack-free, elastic gels are obtained in place of self-adhesive gels.

Preferred polyhydroxy compounds are polyetherpolyols like those mentioned in detail in the abovementioned publications.

Both (cyclo)aliphatic and aromatic isocyanates are suitable as polyisocyanate components. Preferred (cyclo)aliphatic polyisocyanates are 1,6-hexamethylene diisocyanate and its biurets and trimers, and hydrogenated diphenylmethane diisocyanate ("MDI") types. Preferred aromatic polyisocyanates are those obtained by distillation, such as MDI mixtures of 4,4' and 2,4' isomers or 4,4'-MDI, and tolylene diisocyanates ("TDI") types.

The diisocyanates may be chosen in particular for example from the group of unmodified aromatic or aliphatic diisocyanates or else from modified products formed by prepolymerization with amines, polyols or polyetherpolyols.

The polyurethane xerogel matrix may be employed partly or full-area foamed and/or unfoamed, unfilled or with additional fillers such as, for example, superabsorbents, titanium dioxide, zinc oxide, plasticizers, dyes etc. For applications in the field of scar reduction it is additionally possible to use hydrogels in semisolid to solid form with active constituents for the central zone.

The polyurethane xerogels may, where appropriate, comprise additives known per se from polyurethane chemistry, such as, for example, inorganic- or organic-based fillers and short fibers, metal pigments, surface-active substances or liquid extenders such as substances having a boiling point above 150° C. Examples of organic fillers which may be mentioned are barytes, chalk, gypsum, kieserite, soda, titanium dioxide, cerium oxide, quartz sand, kaolin, carbon black and hollow microspheres.

Organic fillers which can be employed are, for example, powders based on polystyrene, polyvinyl chloride, urea-formaldehyde and polyhydrazodicarbonamide. Suitable short fibers are, for example, glass fibers with a length of 0.1–1 mm or fibers of organic origin, such as, for example, polyester or polyamide fibers. Metal powders such as, for example, iron or copper powder can likewise also be used in the gel formation. In order to confer the desired color on the gels, the organic- or inorganic-based dyes or color pigments known per se for the coloring of polyurethanes can be used, such as, for example, iron oxide or chromium oxide pigments, phthalocyanine- or monoazo-based pigments. Examples of surface-active substances which may be mentioned are cellulose powder, activated carbon and silica products.

The adhesive properties of the gels can be modified by adding where appropriate additions of polymeric vinyl compounds, polyacrylates and other copolymers customary in adhesives technology, or else adhesives based on natural substances up to a content of 10% by weight based on the weight of the gel composition.

The polyurethane xerogel layer is, in particular, transparent, water vapor-pervious and adhesive. This represents a significant advantageous difference from the scar contact materials based on silicone gel. The transparency additionally increases the acceptance by the user because a scar-reducing plaster is normally worn on the skin over a lengthy period.

It is possible and preferable to incorporate a superabsorbent polymer as powder for storage of fluid. Preferred water-absorbing materials are water-absorbing salts of polyacrylates and copolymers thereof, which are known as superabsorbents, in particular the sodium or potassium salts. They may be uncrosslinked or crosslinked and are also obtainable as commercial products. Particularly suitable products are those disclosed in DE 37 13 601 A1, and also superabsorbents of the new generation which now have only small contents of water removable by drying and high swelling capacity under pressure.

Preferred products are slightly crosslinked polymers based on acrylic acid/sodium acrylate. Sodium polyacrylates of this type are obtainable as Favor 22-SK (Stockhausen & Co. KG., Germany). Further absorbents, for example carboxymethylcellulose and karaya, are likewise suitable.

It is therefore advantageous to incorporate superabsorbent or a superabsorbent polymer in an amount of from 0.01 to 30% by weight, in particular from 0.5 to 25% by weight, in particular 10% by weight, based on the total mass of the polyurethane xerogel matrix, into the scar contact material.

Polyurethanes prove to be extremely advantageous compared with other adhesive materials such as polyacrylates, rubber, etc. since they entail no known potential for allergy and, especially in contrast to polyacrylates, have no hyperallergenic action.

The essential advantages of the use according to the invention of the scar-reducing plaster derive, however, from the different mechanisms of action which are explained in detail below.

a. It is known that an increase in temperature promotes collagenase activity and thus new tissue formation. It has been demonstrated in various tests that thermal insulation of the scar takes place on application of the scar plaster of the invention. Hence there is a sensitive increase in temperature, and the collagenase is advantageously stimulated.

b. Owing to the pressure of the scar-reducing plaster on the scar surface, a directed collagen fiber formation is assisted, thus reducing or entirely preventing the formation of hyperthropic scars. The plaster acts like actual skin.

c. Owing to the high water vapor perviousness of the plaster of the invention, moisture released from the skin is removed, and the underlying layer of skin is not softened. The result is that the scar-reducing plaster of the invention is very comfortable to wear since, in particular, the wearing time may extend over a lengthy period from a few days up to several weeks.

d. The adhesiveness of the polyurethane xerogel matrix employed can be varied in such a way that the adhesiveness is reduced or entirely abolished on contact with water. This means on the one hand that the adhesiveness can be adjusted to be high during the wearing time and, at the same time, painless detachment without residues is possible after wearing. For removal of the plaster, the user needs merely to pull it off under the faucet. This means that the plaster of the invention is even more kindly to the skin because the skin is not stressed on detachment, i.e. the topmost layers of skin, corneocytes, are pulled off to a smaller extent.

Figure 2:
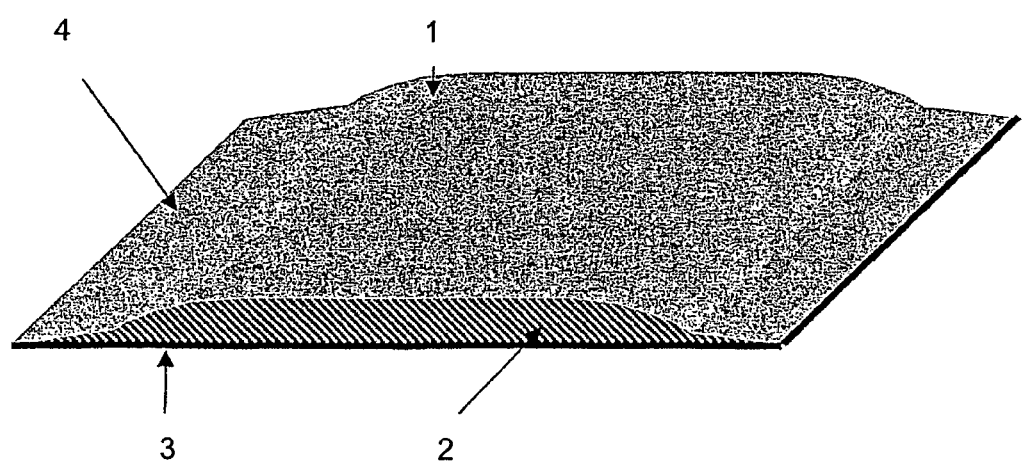
FIG. 2 provides another embodiment of the present invention wherein the scar-reducing plaster is beveled toward the edge.
Figure 3:
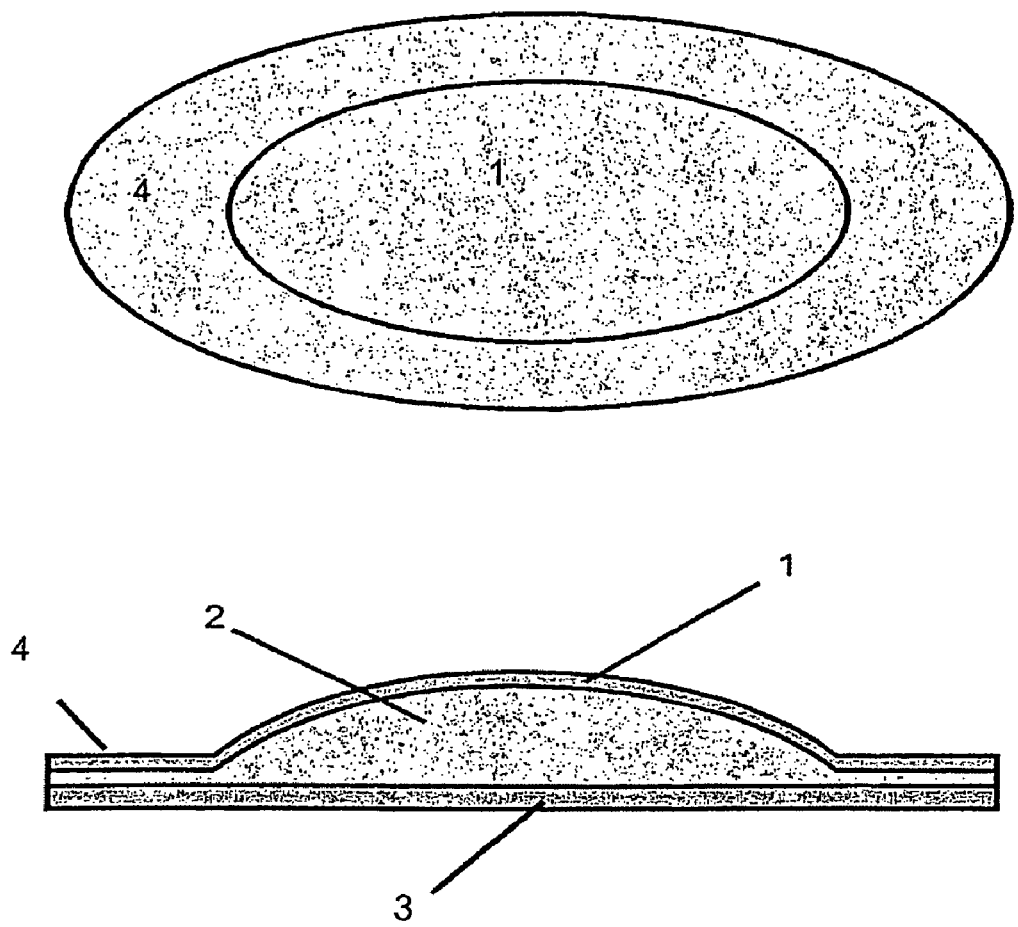
FIG. 3 provides yet another embodiment of the present invention wherein the scar-reducing plaster has a beveled edge over the entire periphery.

The scar-reducing plaster of the present invention can be further described with reference to the figures. FIG. 1 shows the simplest embodiment of the invention comprising a covering material (3) and a backing film (1) whose whole area is coated with the polyurethane xerogel matrix (2). FIG. 2 shows a scar-reducing plaster beveled towards the edge (4). FIG. 3 shows a scar-reducing plaster having a beveled edge layer (4) over the entire periphery.

The scar-reducing plaster of the invention can include an edge layer of polyurethane xerogel matrix as depicted in FIG. 2, in which case the scar contact material and the edge layer consist of the same polyurethane xerogel matrix, and the edge layer is beveled to a thickness not exceeding 5 to 150 µm, in particular 30 to 90 µm, at the edge.

This has the advantage that the plaster greatly reduces the tendency of usual plasters to peel off, caused by clothing, bed sheets, skin contact or during washing. This in turn makes it possible for the first time for the scar plaster to be worn for the long duration of scar treatment without additional fixings.

The scar-reducing plaster may have an elongate shape which can be rolled up and cut to any length. It has the advantage that the user can cut from the roll a plaster in one piece which is appropriately adapted to the individual length of the scar.

For better, more sterile transport and storage of the plaster, it can be provided with a protective covering on the adhesive side, which is removed before the plaster is placed on the skin. This may be, for example, siliconized paper or an especially siliconized film, so that the adhesive side is protected during storage.

The plaster of the invention is to be used as scar-reducing plaster.

A further advantage of the plaster of the invention is the production of the scar contact material with/without edge layer of a piece. Continuous mergings which allow a variable shape and size of the plasters on production results. Thus both the anchoring of the polyurethane xerogel layer on the backing and the adhesion to the skin is improved.

The scar contact material is thus located in the center and merges continuously with the edge layer.

The process for producing the scar-reducing plaster proceeds simplified via three stages, where:

a) a layer of a polyurethane xerogel is applied to an intermediate backing;

b) the uncured polyurethane xerogel on the intermediate backing and a backing film are laminated together in particular by a knife; and c) the laminate is then fed into a nip where the polyurethane is rolled out into the final plaster shape with the desired edge layer.

The nip can be formed by a smooth roll and a contoured roll. Or else the contouring takes place after the lamination by means of a downstream contoured roll.

The contoured roll has recesses which ensure production of convex plaster shapes which become thinner steadily towards the edge.

The production process makes it possible to produce, according to the invention, monolayer or multilayer products which naturally have three-dimensional contours. The scar contact material area may moreover correspond to a conventional shape (a raised, for example, rectangular wound contact material applied to the backing material (see FIG. 1) or, for example, have a lenticular curvature with a shape which is convex to the outside, or from combined convex and concave elements, with the area facing the scar being flat.

Various impressions (recesses) may be present in the contoured roll in order to achieve shaping of the polyurethane layer. For example, they may have the shape of a semiconvex lens. This leads to elevated centers in the polyurethane layer, which are beveled towards the edge. Also possible are ellipsoids, cuboids, cubes or other geometric shapes in order to generate specific shapes in the polyurethane layer. The contouring profile from the center to the edge is fixed by the chosen shape, meaning that the contoured roll determines the design of the contour.

The geometries of the contoured shaped articles which can be produced are diverse (round, elliptical, rectangular, triangular, etc.).

For the treatment, lamination of the polyurethane xerogel layer it is possible to generate a pressure of from 1 bar to 10 bar, in particular 5 bar, in the nip. In addition, the nip should have dimensions such that the polyurethane xerogel layer has a thickness of from 0.2 to 2 mm, in particular from 0.5 to 1.5 mm.

The process allows, according to the invention, production in a continuous process. It is thus also possible to generate potential savings in the process energy and the capital costs for plant.

The described embodiments, illustrated by FIGS. 1 to 3, make the present invention clear without restricting it. The stated numerical values mean percentages by weight based on the total weight of the particular preparations, unless otherwise indicated.

That which is claimed:

1. A scar-reducing plaster, comprising
   a backing film comprising an air- and water vapor-pervious and water-impervious polymer layer, and
   a breathable and adhesive polyurethane xerogel matrix layer coating the backing film, the polyurethane xerogel matrix layer including a central scar contact region and an edge region, wherein the scar contact region merges with the edge region and the thickness of the edge region decreases from the scar contact region to a thickness of from 5 to 150 µm at the edge of the polyurethane xerogel matrix layer.

2. The scar-reducing plaster as claimed in claim 1, wherein the thickness of the edge region decreases from the scar contact region to a thickness of from 30 to 90 µm at the edge of the polyurethane xerogel matrix layer.

3. The scar-reducing plaster as claimed in claim 1, wherein the plaster has an elongate shape which can be rolled up and cut to any length.

4. The scar-reducing plaster as claimed in claim 1, wherein the edge region is disposed around the entire periphery of the plaster.

5. The scar-reducing plaster as claimed in claim 1, wherein the backing film comprises one or more polymers selected from the group consisting of polyurethane, polyethylene, polypropylene, polyamide, polyester and polyether-polyester.

6. The scar-reducing plaster as claimed in claim 1, wherein the plaster is transparent.

7. The scar-reducing plaster as claimed in claim 1, wherein the polyurethane xerogel matrix adheres on contact with water.

8. The scar-reducing plaster as claimed in claim 1, wherein the scar contact region has a thickness of from 0.2 to 2 mm.

9. The scar-reducing plaster as claimed in claim 8, wherein the scar contact region has a thickness of from 0.5 to 1.5 mm.

10. The scar-reducing plaster as claimed in claim 1, wherein the polyurethane xerogel matrix comprises a superabsorbent polymer present in an amount of from 0.01 to 30% by weight based on the total weight of the polyurethane xerogel matrix.

11. The scar-reducing plaster as claimed in claim 10, wherein the superabsorbent polymer is present in an amount of from 0.5 to 25% by weight, based on the total weight of the polyurethane xerogel matrix.

12. The scar-reducing plaster as claimed in claim 11, wherein the superabsorbent polymer is present at 10% by weight, based on the total weight of the polyurethane xerogel matrix.

13. The scar-reducing plaster as claimed in claim 1, wherein the polyurethane xerogel matrix is in partly foamed form.

14. The scar-reducing plaster as claimed in claim 1, wherein the polyurethane xerogel matrix is in full-area foamed form.

15. The scar-reducing plaster as claimed in claim 1, wherein the thickness of the edge region decreases continuously from the scar contact region to the edge of the polyurethane xerogel matrix layer.

16. A method for treating a hypothropic scar, said method comprising applying to the hypothropic scar a scar-reducing plaster, wherein the plaster comprises:
   a backing film comprising an air- and water vapor-pervious and water-impervious polymer layer, and
   a breathable and adhesive polyurethane xerogel matrix layer coating the backing film, the polyurethane xerogel matrix layer including a central scar contact region and an edge region, wherein the scar contact region merges with the edge region and the thickness of the edge region decreases from the scar contact region to a thickness of from 5 to 150 µm at the edge of the polyurethane xerogel matrix layer.

* * * * *